United States Patent [19]
Narciso, Jr.

[11] Patent Number: 5,217,456
[45] Date of Patent: Jun. 8, 1993

[54] DEVICE AND METHOD FOR INTRA-VASCULAR OPTICAL RADIAL IMAGING

[75] Inventor: Hugh L. Narciso, Jr., Santa Barbara, Calif.

[73] Assignee: PDT Cardiovascular, Inc., Goleta, Calif.

[21] Appl. No.: 840,478

[22] Filed: Feb. 24, 1992

[51] Int. Cl.$^5$ ............................................. A61B 17/32
[52] U.S. Cl. ........................................ 606/15; 606/17; 606/7; 606/16
[58] Field of Search ...................... 606/2, 3, 7, 13–18; 128/395–398

[56] References Cited

U.S. PATENT DOCUMENTS

| | | | |
|---|---|---|---|
| 4,768,858 | 9/1988 | Hussein | 606/7 X |
| 4,850,351 | 7/1989 | Herman et al. | 606/16 X |
| 4,860,743 | 8/1989 | Abela | 606/16 |
| 4,917,084 | 4/1990 | Sinofsky | 606/16 X |
| 4,993,412 | 2/1991 | Murphy-Chutorian | 606/7 |
| 5,032,123 | 7/1991 | Katz et al. | 606/15 |

Primary Examiner—Peter A. Aschenbrenner
Attorney, Agent, or Firm—Michael G. Petit

[57] ABSTRACT

An intra-vascular optical radial imaging system comprising an intra-vascular guidewire-compatible catheter, a source of illumination and a synchronous fluorescence detector. The catheter is inserted into a blood vessel until the tip is adjacent to a section of vessel to be imaged. A narrow beam of light emanating radially from an aperture underlying the segment to be imaged repetitively illuminates segments of the wall of the vessel in a scanning or sweeping manner with the light of a wavelength that induces fluorescence in molecules in the tissue. Fluorescence from molecules in the illuminated tissue enters the catheter through the aperture and is conveyed to a spectral analyzer. Properties of the fluorescence signal are characteristic of the particular tissue and may be used to differentiate healthy tissue from atherosclerotic plaque. The method yields not only the longitudinal position of a lesion along a vessel but also the cylindrical coordinates by determining the circular or angular position of the lesion on the interior wall of the vessel.

7 Claims, 5 Drawing Sheets

DEVICE AND METHOD FOR INTRA-VASCULAR OPTICAL RADIAL IMAGING

BACKGROUND OF THE INVENTION

1. Field of the Invention

The present invention provides a method and apparatus for optically imaging the inner wall of a tubular tissue and more particularly, provides an intra-vascular device for the optical imaging of plaque and the like on the inner wall of a blood vessel.

2. Description of the Prior Art

Interventional catheter-based therapeutic techniques have recently become important as they may avoid the necessity of less conservative surgical procedures. Techniques to widen a luminal obstruction in an artery include balloon dilation, tip abrasion, atherectomy, photodynamic therapy and laser ablation.

The primary limitation in choosing the appropriate therapeutic modality for cardiovascular intervention is a lack of information about the vessel being treated. Visualizing the extent of the disease and guiding an interventional device is severely limited by the present imaging technology. The most commonly employed and least informative modality for vascular imaging is angiography. Newer modalities such as angioscopy, spectroscopy, extravascular ultrasound, and intra-vascular ultrasound have shown varying degrees of success.

Angiography provides a two-dimensional blood flow map. A radiopaque dye is injected into the vessel being visualized and x-ray fluoroscopy indicates the path of the dye flow as a dark projection. Angiography does not give information about the vessel but indicates the remaining open lumen. Angiography only shows the border between the blood and the innermost surface of the vessel. If blood flow is completely occluded, angiography is useless. Since this process is a two-dimensional view of the vessel, an occluded vessel may appear completely open in one projection while a 90-degree rotation of the projection would clearly show a severely occluded vessel.

Angioscopy employs a small diameter low profile highly flexible endoscope. Angioscopy only supplies information of the luminal surface. Such topographical information is marginally useful at best. For angioscopy to function, the optical pathway between the imaging device and the vessel wall must be clear. This is achieved by either large volumes of saline flush or by total occlusion of the vessel. Small quantities of saline flush will not clear the vessel adequately for this procedure. Large quantities of saline flush can (a) cause an electrolyte imbalance leading to congestive heart failure or (b) cause ischemia due to a lack of perfusion of oxygen rich blood to muscles. If the arteries being treated are the coronaries, prolonged ischemia in the heart is not always well tolerated. Again, in a total occlusion, angioscopy is useless.

Spectroscopy to differentiate diseased and healthy tissue has had limited success in so-called "smart laser" systems. These devices have employed bundles of fibers to detect atheromatous plaques. The technology has been limited by the small number of fibers employed as discrete detectors. This geometry relays information which is too segmented and often conflicting to be useful in the decision-making process.

Extravascular ultrasound vessel imaging or color flow Doppler imaging has been used for quite some time. The information provided is of a gross nature not generally applicable as a detailed imaging or guidance system. The technology is based on the concept that there is a frequency shift in reflected ultrasound waves which may be used to measure flow velocity. Color flow Doppler is very useful for detecting flow conditions non-invasively, but cannot provide the detailed information necessary for intra-vascular applications.

Intra-vascular ultrasound (IVUS) has gained in popularity in the past few years. IVUS goes beyond angiography and angioscopy by supplying information below the intimal surface of the vessel to create a computer generated cross-sectional view of the vessel which can be displayed on a video monitor. The architecture of the vessel including intima, media, and adventitia along with atheromatous plaques and calcified lesions is well defined and easily observed.

In view of the detailed information from IVUS it is advantageous to develop an analogous optical system. An intravascular optical radial imaging (IVORI) system supplies both topographical and subintimal radial information on the composition of a vessel which can be displayed as a cross-sectional view or as a 3-dimensional reconstruction of the vessel. Such data provides realtime high resolution information about the vessel architecture to: (a) indicate diseased and healthy parts of the vessel, (b) guide an interventional therapy such as Percutaneous Transluminal Coronary Angioplasty (PTCA) or laser angioplasty, (c) guide an interventional therapy such as atherectomy which works best in eccentric lesions (which are not always visible and locatable under fluoroscopy), and (d) help the clinician in the decision-making process.

SUMMARY OF THE INVENTION

An IVORI system is described which is an optical analog to the IVUS system; replacing the sonic signal with an optical signal. A single guidewire compatible intravenous catheter with a diffusing tip at its distal end is used as both the excitation source and the sensing source. Surrounding the diffusing tip is an opaque sheath with a window. The proximal end of the sheath is coupled to a motor which is employed to spin the sheath. The spinning motion of the proximal end of the sheath translates to the distal portion of the catheter thus rotating the sheath window at a continuous rate. While the sheath is spinning, the optical fibers are transmitting pulsed light to the diffusing tip where it is scattered. The scattered light exits the window radially, interacts with the tissue, and various wavelengths of fluorescence light return to the catheter which are transmitted back along the catheter to the proximal end via the same optical fibers.

This return signal enters a spectral analyzer where it is separated into various wavelengths which indicate the composition of the vessel. Fibrous plaque fluoresces at a different wavelength from fatty plaque; both of which being different from healthy vessel. Calcified plaques will tend to reflect the excitation wavelength. The intravenous injection of an endogenous or exogenous chromophore which is selectively retained by the proliferating smooth muscle cells of atheromatous plaques may be used to enhance this process. The position of the catheter in the vessel and the angular fluorescence pattern enable the determination of the cylindrical coordinates of an atherosclerotic lesion.

The intensities of the individual wavelengths are detected and coupled to a video system. The video image provides a real-time, high resolution cross-sectional view of the artery being investigated comparable to an IVUS system. Future improvements in software will provide three-dimensional reconstructed views of the lumen.

It is, therefore, an object of this invention to provide an intra-vascular catheter and system for determining the cylindrical coordinates of particular fluorescent molecules on the interior wall of a vessel.

It is another object of this invention to provide a catheter and system to characterize atherosclerotic plaque on the wall of a vessel.

It is yet another object of this invention to provide a method for imaging the cross-sectional view of a blood vessel or like luminal organ.

BRIEF DESCRIPTION OF THE DRAWINGS

A better understanding of the present invention will be gained upon reference to the following detailed description which, when read in conjunction with the accompanying drawings, wherein like reference characters refer to like parts throughout the figures and in which.

DESCRIPTION OF THE PREFERRED EMBODIMENT

Figure 1:
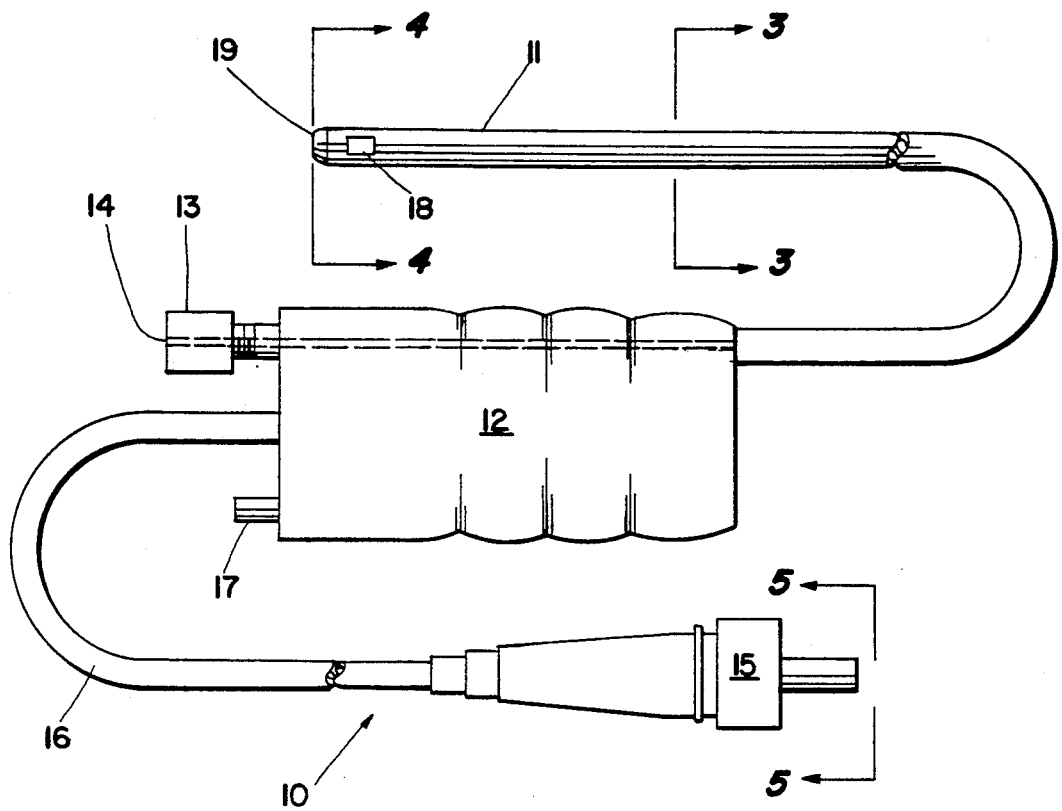
FIG. 1 is a schematic view of the Intra-Vascular Optical Radial Imaging system of the present invention.

FIG. 1 shows an intra-vascular optical radial imaging system generally indicated at the arrow 10. The system comprises a intra-vascular catheter 11 having a distal portion terminating in a beveled tip 19 and a proximal end terminating in a handpiece 12. The handpiece 12 houses the driving motor for a spinning opaque tube, the tube having a slit or aperture in its wall, and is where the individual fibers comprising the fiber bundle 16 carrying light from a source (not shown) to the intra-vascular catheter 11 are separated and rearranged to form a circular array inside of a cylindrical tube. The handpiece 12 also houses a hemostasis valve 13 with a guidewire lumen 14 passing therethrough. In practice, a guidewire (not shown) is inserted into a blood vessel of the patient and advanced until the distal tip of the guidewire is distal to a segment of the vessel under study. The distal beveled tip 19 of the intra-vascular catheter 11 is then inserted over the guidewire and advanced into the vessel until the distal tip of the intra-vascular catheter is near the region to be studied. The proximal end of the guidewire exits the handpiece through the hemostasis valve 13. Light from a source (not shown) enters the fiber bundle 16 through the connector 15 to pass into the handpiece. In the handpiece the fiber bundle is opened and the individual optical fibers comprising the bundle are rearranged into an annular array to form a tubular member and are incorporated within the intra-vascular catheter 11.

Figure 2:
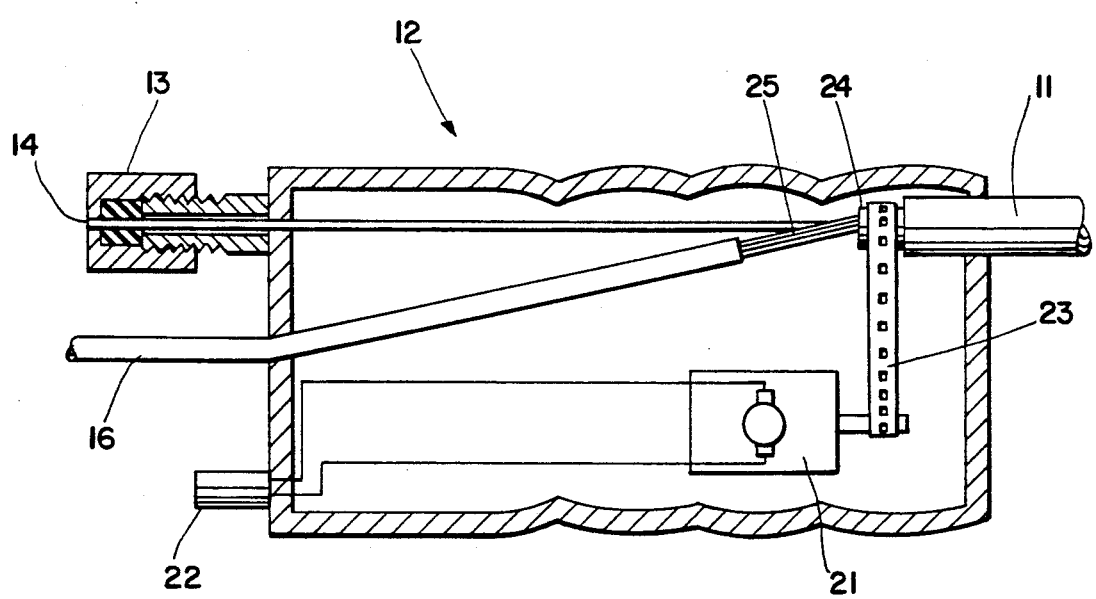
FIG. 2 is a schematic view of the handpiece showing the mechanical drive in relationship to the overall system.

The handpiece and its internal components are shown in more detail in FIG. 2. The transparent outer sheath of the intra-vascular catheter 11 is stripped back to expose an opaque sheath 24 which is capable of rotation within the intra-vascular catheter 11. The opaque sheath 24 has means thereon for engaging a drive member 23 which is driven by a motor 21 thereby causing the sheath to rotate within the catheter 11. The on/off condition and speed of the motor 21 is controlled by a power source 22. The fiber optic bundle 16 enters the handpiece and the outer sheath is stripped away so that the optical fibers can be rearranged into an annular array to surround a central core member within the intra-vascular fiber. The guidewire lumen 14 extends through the hemostasis valve and handpiece and forms the central lumen of the central core of the intra-vascular catheter as shown in FIG. 3.

Figure 3:
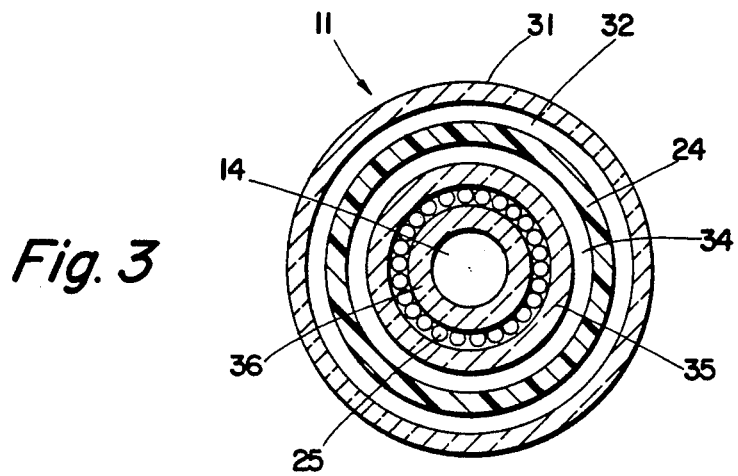
FIG. 3 is a cross-sectional view of the treatment catheter of FIG. 1 along line 3—3.

FIG. 3 shows the intra-vascular catheter in more detail. The cross-section of the intra-vascular catheter 11, taken along line 3—3 of FIG. 1 shows the various concentric tubular members comprising the intra-vascular catheter body portion. The intra-vascular catheter body portion consists of an outer transparent sheath 31 which directly overlies an annular space 32. Underlying the annular space 32 is a opaque spinning tube 24. The opaque spinning tube 24 has a slit, or aperture, cut therein (not shown) near the distal end. Directly underlying the opaque spinning tube is a second air space 34 and underlying the second air space is a transparent sheath 35. The transparent sheath 35 permits the passage of light emanating from the optical fiber array 25 to exit into the space between the transparent sheath 35 and the opaque sheath 24. Directly underlying the annular fiber array 25 is a reflective core member 36 which comprises a reflective tube with a central lumen forming the guidewire lumen 14. These elements will be shown in more detail as we proceed but first let's look at more general characteristics of the catheter and the light source.

Figure 4:
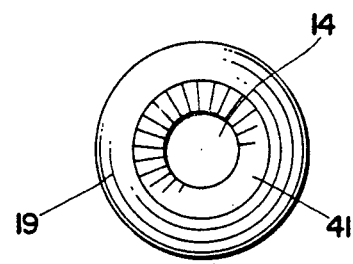
FIG. 4 is an end view of the treatment catheter of FIG. 1.
Figure 5:
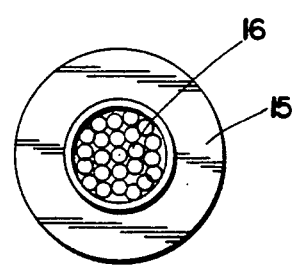
FIG. 5 is an end view of the optical connector along line 5—5 of FIG. 1.

FIG. 4 shows the distal tip of the intra-vascular catheter with the beveled tip portion 19, a guidance wire introducer funnel portion 41, and the central guidewire lumen 14. The funnel-shaped guidewire introducer funnel 41 facilitates the insertion of the intra-vascular catheter 11 over a guidewire once the guidewire is in position. As shown in FIG. 5, the illuminating source (not shown) enters the fiber bundle 16, which is housed within an optical connector 15.

Figure 6:
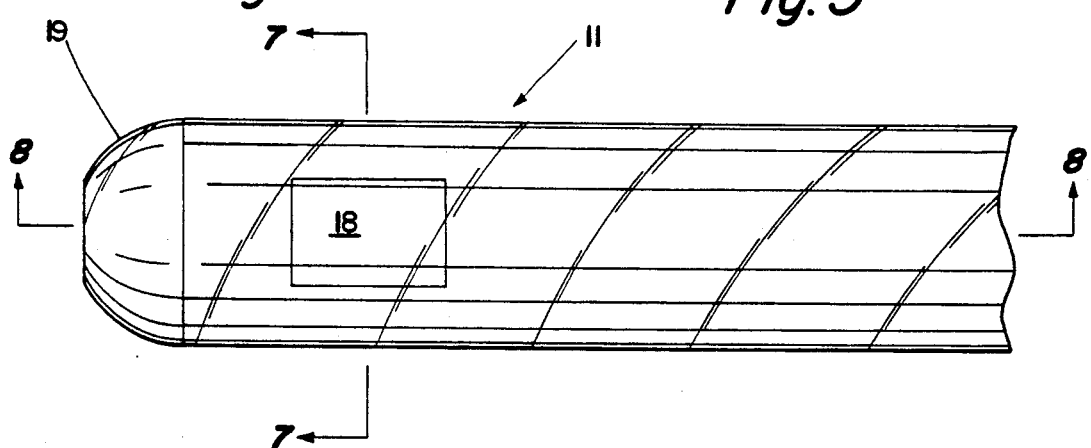
FIG. 6 shows an elevational view of the distal tip of the treatment catheter.
Figure 7:
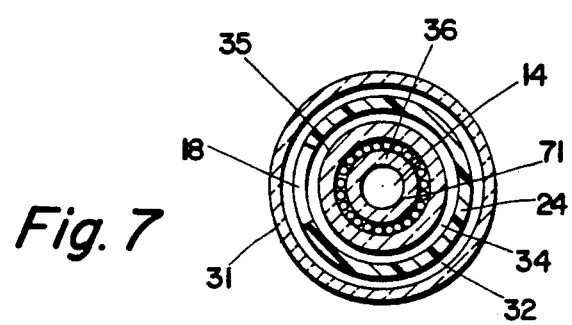
FIG. 7 is a cross-sectional view of the treatment catheter of FIG. 6 taken along line 7—7.

In FIG. 6, the distal end of the intra-vascular catheter 11 is shown in larger scale. This plan view shows the slit or aperture 18, and the beveled tip 19. FIG. 7 shows yet another sectional view of the tubular members comprising the intra-vascular catheter along line 7—7 of FIG. 6 which section line cuts through the slit 18 on the opaque spinning tube 24. In FIG. 7, the outer transparent sheath 31 overlies the annular air space 32. Directly underlying the annular air space 32 is the opaque spinning tube 24 with a window or slit 18 cut therein. Underneath the slit is a second air space 34 which separates the spinning tube 24 from a second transparent sheath 35 which surrounds the diffuser tip 71 of the optical fiber array 25. The diffuser tip 71 of the optical fiber array 25 comprises a tubular silicone member containing scattering centers embedded therein, the diffuser tip receiving light from individual fibers 82 (FIG. 8) in the fiber array 25. Of course, any member suitable for diffusing light out through the aperture 18 could be used but the material in which the scattering centers are embedded should be optically transparent at the illuminating wavelengths and non-absorbing at the fluorescence wavelengths. Light traveling down the optical fiber array 25 encounters scattering centers embedded in the diffuser tip 71 and scatters light radially outward. All but a portion of the scattered light is blocked by the spinning opaque tube. The unblocked portion of the scattered light passes through the aperture or slit 18 and exits the intra-vascular catheter through the transparent sheath 31. Thus, the opaque spinning tube 24 with the aperture 18 therein, provides a rotating slit of illumination to illuminate the walls surrounding the intra-vascular catheter. The light exiting the catheter through the aperture 18 interacts with chromophore molecules in the tissue on the wall of the blood vessel to produce a fluorescent signal. If the tissue on the wall of the vessel contains chromophores which may be either endogenous or exogenous, the tissue may fluoresce in a manner characteristic of the chromophore present. Such fluorescence enters the intra-vascular catheter through the aperture 18 whence it passes to the diffuser tip portion 71 which is in optical communication with the individual fiber(s) 82 abutting the portion of the diffuser portion 71 immediately underlying the aperture 18 and passes back up the catheter towards the handpiece 12. Analysis of this fluorescent light may be used to characterize the tissue surrounding the catheter and correlation of the fluorescence signal with slit position will provide a radial image showing the exact position of the lesion on the wall of the vessel.

Figure 8:
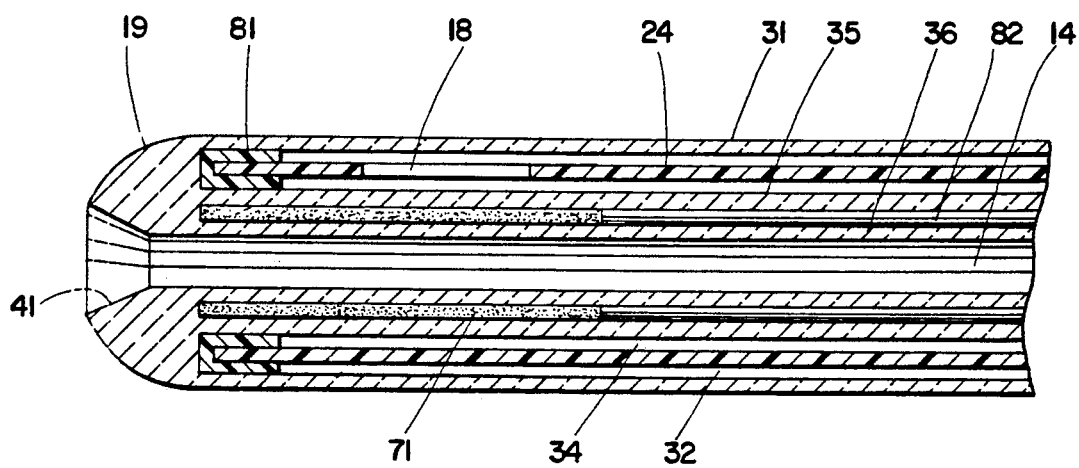
FIG. 8 is a longitudinal cross-sectional view of the distal tip of the treatment catheter of FIG. 6 taken along line 8—8.

A longitudinal cross-sectional view of the distal and body portion of the intra-vascular catheter 11 is shown in more detail in FIG. 8. The outer transparent sheath 31 thickens and tapers down to meet the central reflective core 36 and form the beveled tip 19 of the catheter. The beveled tip 19 of the catheter 11 in turn, has a funnel-shaped orifice therein generally indicated at 41, which funnel shape facilitates the introduction of a guidewire (not shown) into the guidewire lumen 14 of the intravascular catheter 11. A Teflon bearing spacer 81 spaces the opaque spinning tube 24 from both the outer sheath 31 and the underlying transparent sheath 35 and reduces friction so that the spinning tube may spin more easily. Light enters the intra-vascular vascular catheter through the individual optic fibers, one of which is shown at 82, which individual optical fibers comprise the annular fiber array 25, and travels from right to left. The light travels along the optical fiber 81 until it encounters the diffuser tip 71 at which point it is radially scattered. The light that is scattered inward is reflected outward by the reflective core member 36. The radially scattered light traveling outward is either absorbed by the opaque spinning tube 24 or it may pass through the aperture 18. That light passing through the slit 18 is the light that interacts with molecules in the tissue in the wall of the blood vessel. The slit, as mentioned earlier, also provides the entrance portal for fluorescent light from molecules in the tissue surrounding the intra-vascular catheter. As mentioned earlier, the spectral composition of the fluorescent re-entering the intra-vascular catheter 11 through the slit or aperture 18 then passes back into the handpiece through specific optical fibers within the optical fiber array 25 where they are received and analyzed for their spectral composition as is discussed elsewhere (see, for example, "Discrimination of Normal and Atherosclerotic Aorta by Laser-Induced Fluorescence" L. I. Deckelbaum, et al, Lasers in Surgery and Medicine 7:330–335 (1987)).

Figure 9:
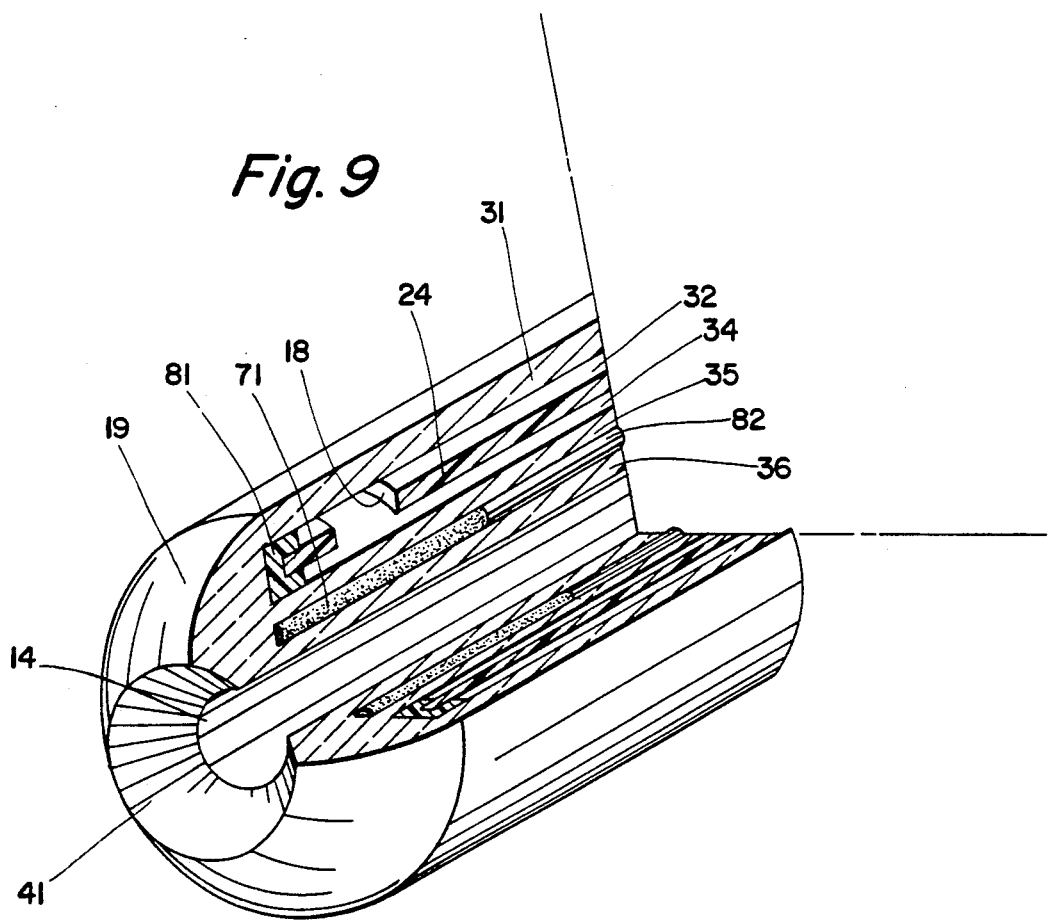
FIG. 9 is a partially cutaway perspective view of the distal end of the intraluminal catheter.

FIG. 9 is yet another partially cut away perspective view of the intra-vascular catheter 11 showing the tubular components thereof with respect to one another. The central core 36 of the intra-vascular catheter 11 ends in a funnel-shaped orifice 41 which narrows down to form the guidewire lumen 14. Thus, the funnel-shaped orifice 41 is the distal end of the guidewire lumen 14 within the reflective core of the catheter. Surrounding the reflective core 36 is the annular array 25 of individual optical fibers 82 with diffuser tips 71 thereon. Immediately surrounding the diffuser tip is the transparent sheath 35 and the opaque spinning tube 24. The outer sheath 31 completes the catheter.

In the above-described preferred embodiment of the IVORI catheter, several options for materials for the various components exist. The key parameters are optical transparency, flexibility and strength. Materials such as high strength polyester and polyethylene terephthalate (PET) are very clear and easily extruded in ultrathin wall sizes. A high strength braided polyester is useful for translating the spinning motion over a long distance. The spacer/bearing can be made from Teflon ® which is very lubricious. The overall flexibility of the catheter is approximately the same as similar sized cardiovascular laser catheters which are loaded with larger core stiff fiber optics and are deliverable to small diameter tortuous coronary arteries.

The size of the catheter from the inside out is as follows: The guidewire lumen must be sufficiently large to accommodate an 0.018" guidewire; therefore, the lumen should be 0.022". The wall thickness of the guidewire lumen should be at least 0.002" making the O.D. 0.026" nominal. The fiber optics are 100 micrometer core. With two layers on the O.D., the diameter at this point is 0.036" nominal. The tube outside of the fiber should again have a wall thickness of 0.002" making the total O.D. at this point 0.040" nominal. The two air spaces will be 0.005" each; therefore on the cross section will add 0.020" to the O.D. Between these air spaces is the braid (opaque spinning tube) with the aperture therein. The opaque spinning tube is conveniently fabricated of braided polyester having a thickness of 0.005" and thus add 0.010" to the diameter. Adding the braid and the air space to the previously calculated O.D., the O.D. at this point is 0.060" nominal. The outer sheath can again be very thin walled material (0.002") making the total O.D. of the catheter 0.064" nominal. That is slightly larger than 1.5 mm which will access most vessels in the body except for some distal coronaries and vessels below the knee.

Figure 13:
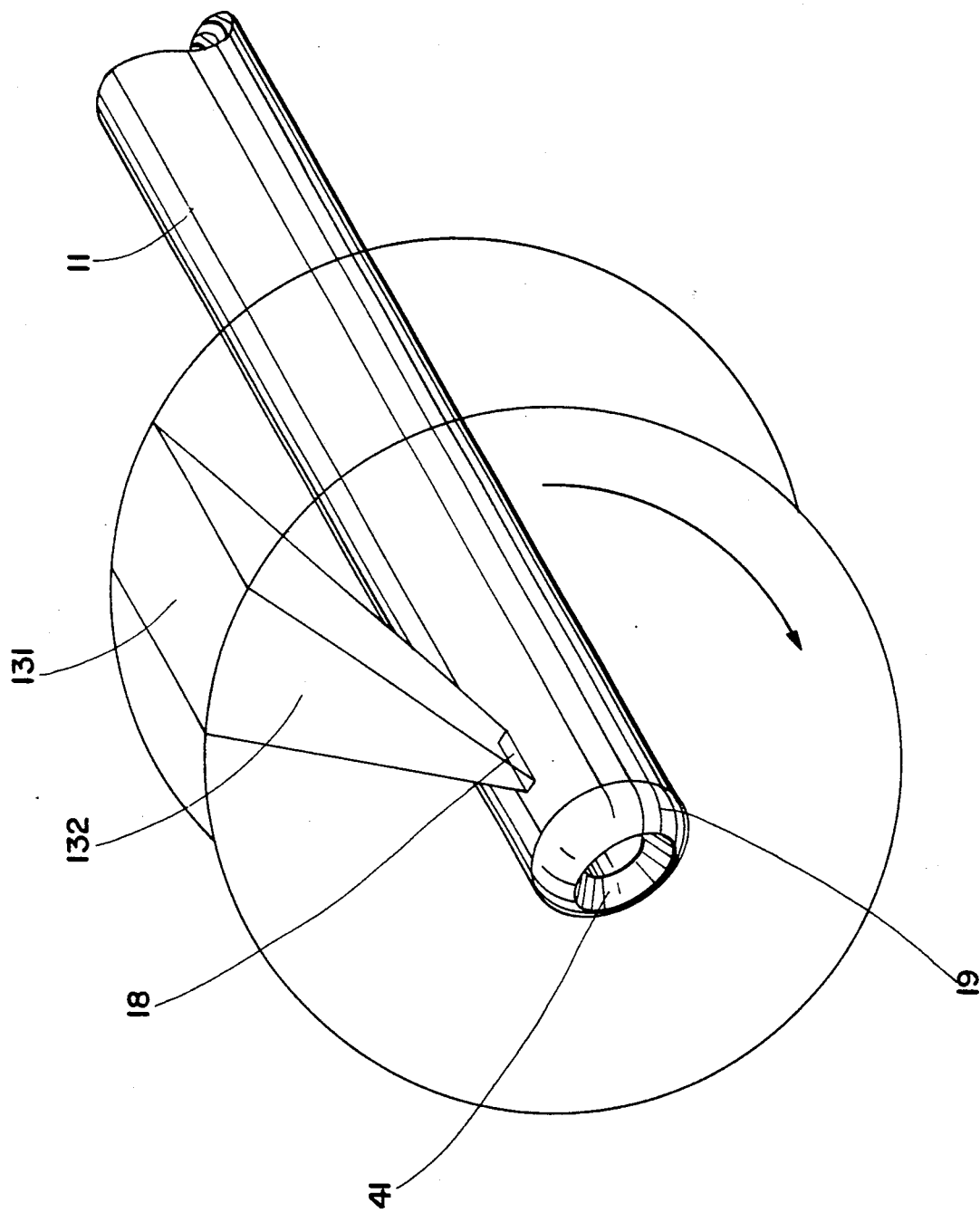
FIG. 13 is a perspective view of the tip of the catheter showing the instantaneous and total field of illumination of the catheter.

FIG. 13 shows illuminating light 131 emitted radially outward from the slit or aperture 18 near the tip of the catheter 11. The light 131 leaving the catheter 11 at an angle 132 which is preferably less than 10 degrees. The wedge of emitted light 131 is swept through 360 degrees as indicated by the arrow at a particular frequency. The wedge of light 131 will be absorbed by chromophore molecules in the surrounding tissue (not shown), inducing them to fluoresce. The fluorescence, which, for the speeds of rotation of the light wedge 131 contemplated herein, can be taken to be instantaneous, is radiated by the chromophores to reenter the catheter 11 through the aperture or slit 18. The fluorescence light, which is characteristic of the chromophore, is scattered back down the individual fibers underlying the aperture 18 (not shown) toward the handpiece where it is detected and analyzed. The wedge of light 131 is swept around the surrounding tissue (not shown) in a circular manner to successively illuminate different portions of the surrounding tissue and collect fluorescence light derived therefrom. Once the cylindrical coordinates of a lesion along the wall of a vessel is known, a treatment light such as a laser may be used to illuminate the lesion, the treatment light being switched on synchronously when the aperture 18 underlies the lesion.

The size of the aperture or aperture 18 should be smaller than the size of any individual fiber in the circular array. The fiber size is 100 microns; therefore the aperture should be approximately 0.005" wide. The length is not critical and will depend solely on the intensity of the return signal.

The spinning motion should be at least 30 times per second for real time monitoring.

Figure 10:
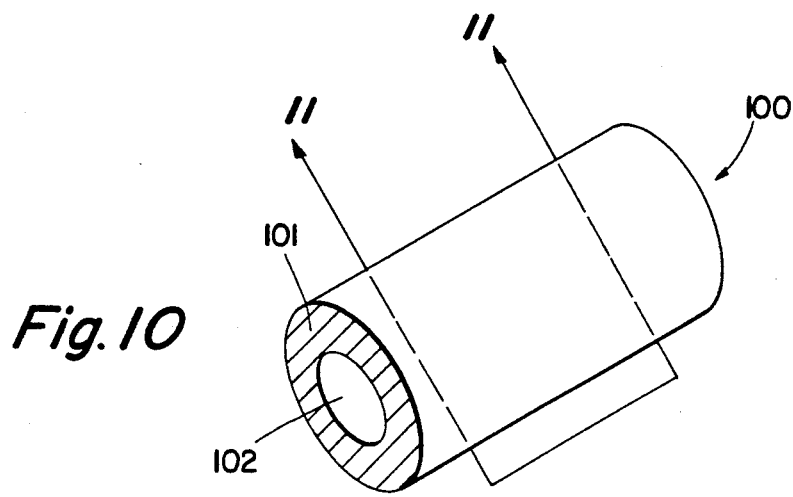
FIG. 10 is a perspective view of a segment of a blood vessel.
Figure 11:
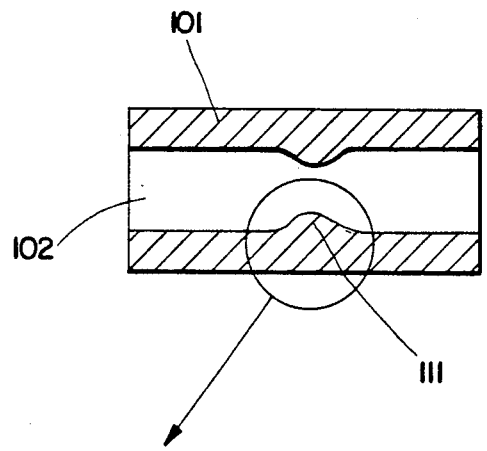
FIG. 11 shows a longitudinal cross-sectional view taken along line 11—11 of FIG. 10 of a segment of a blood vessel containing atherosclerotic plaque.
Figure 12:
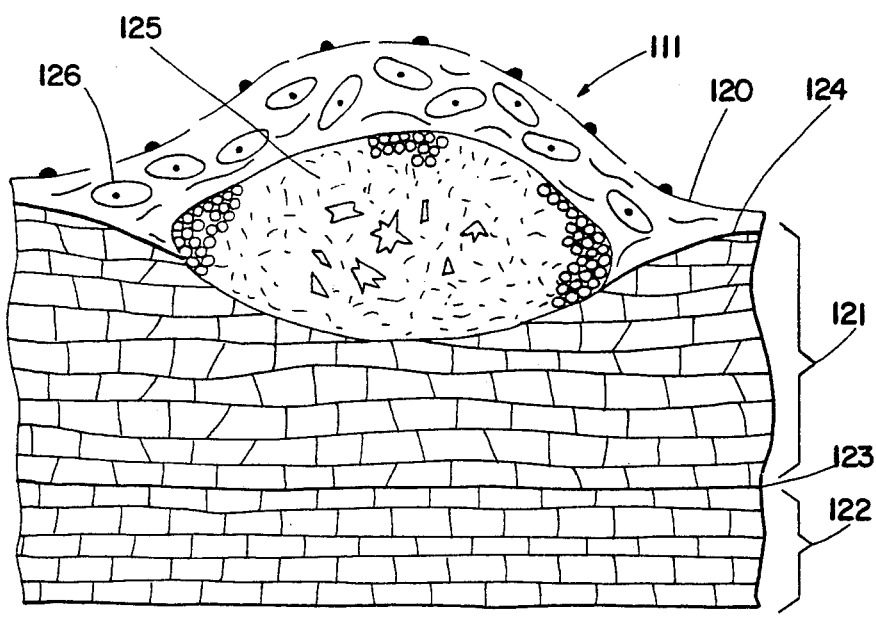
FIG. 12 is an enlarged longitudinal cross-section of the atherosclerotic plaque portion circled in FIG. 11.

As pointed out in the article by L. I. Deckelbaum et al (ibid), analysis of the fluorescent light emanating from chromophore molecules in tissue along the wall of the blood vessel reveals certain features characteristic of particular atherosclerotic plaque on the wall of the vessel. FIG. 10 is a perspective view of a segment of a blood vessel 100 having a wall 101 and a central lumen 102. FIG. 11 shows a longitudinal cross-section of the segment of blood vessel of FIG. 10 bearing an atherosclerotic plaque. The vessel itself comprises an intima 120, a media 121 and adventitia 122 (the tissue overlying the media). The internal elastic lamina 124 separates the intima 120 from the media 121 and the external elastic lamina 123 separates the media 121 from the adventitia 122. The intima 120, when an atherosclerotic plaque, generally indicated at 111, is present, is altered to form a fibrous cap 126 which consists of proliferated smooth muscle cells, collagen, and extracellular and intracellular lipid, including foam cells. The fibrous cap can be dangerous because of its size and its tendency to fracture and ulcerate. The fibrous cap overlies a necrotic center 125 which consists of cell debris, cholesterol crystals, cholesterol esters, and calcium. The necrotic center or core 125 can be dangerous because of its size, its consistency and the thromboplastic substances contained therein. Such plaque takes up chromophores in the blood and retains them longer than normal tissue. Thus, if exogenous or endogenous chromophores are injected into the patient's blood stream and permitted to be taken up by the tissue, the normal tissue will excrete the chromophore before the atherosclerotic plaque will. If exciting light enters the plaque and interacts with the chromophores, it causes such chromophores to fluoresce. The fluorescence can then be analyzed to determine the character and the extent of the atherosclerotic plaque to determine the best therapeutic modality. For example, if the chromophore were a hematoporphyrin or hematoporphyrin derivative, the therapeutic modality might be photodynamic therapy. In such a case the same intra-vascular catheter used to locate and characterize the atherosclerotic plaque could also be used to irradiate it selectively to destroy it.

Although the catheter 11 of the present invention is particularly useful in carrying out in situ imaging of plaque on the wall of the blood vessel, it is understood that it is also useful in other applications in which imaging of tissue along the wall of a luminous structure is desirable. From the foregoing, it will be seen that this invention is one well adapted to attain all the ends and objects hereinabove set forth together with other advantages which are obvious and which are inherent to the structure.

Clearly, the essential feature of the IVORI catheter is the ability to circularly sweep a discrete beam of light over the interior wall of a vessel and gather fluorescence light emitted by molecules in the illuminated area. It is also essential that the system be able to determine the spectral composition of such fluorescence and assign a precise location to the source of such fluorescence. Thus, for example, an IVORI catheter comprising a cylindrical optical fiber array with appropriate guidewire lumen, reflective core and transparent outer sheath could be used. The source of illuminating light could be sequentially coupled into individual fibers conducted to the diffuser tip and radiated outward. The return fluorescence would be most intense in the illuminating fiber underlying the source thereby permitting determination of the circular or angular position of the source of fluorescence on the inner wall of the vessel.

It will be understood that certain features and subcombinations are of utility and may be employed without reference to other features and subcombinations. This is contemplated and is within the scope of the claims. Since many possible embodiments may be made of this invention without departing from the scope thereof, it is to be understood that all matter herein set forth or shown in the accompanying drawings is to be interpreted as illustrative and not in a limiting sense.

Having thus described the invention, I claim:

1. A guidewire compatible intra-vascular catheter for intra-vascular optical radial imaging, at least a portion of said intra-vascular catheter being insertable into a blood vessel, said insertable portion of said catheter comprising a hollow tubular member having a proximal end which receives light from a source of illumination and a distal end, and a central guidewire lumen forming a conduit therebetween, said insertable portion of said intra-vascular catheter further comprising a cylindrical optical fiber array surrounding and coaxial with said guidewire lumen, said array consisting of a multiplicity of individual optical fibers, each fiber terminating in a diffuser tip portion near the catheter's distal end, and means for directing a narrow beam of light from the diffuser tip portion radially-outward to illuminate a target along the wall of the vessel to induce fluorescence in molecules therein, and means for receiving the return fluorescent signal from the tissue.

2. The intra-vascular catheter of claim 1 wherein said distal end is tapered to facilitate entry into a blood vessel.

3. The intra-vascular catheter of claim 1 wherein said means for directing said narrow beam of light radially outward from the diffuser tip comprises a rotatable opaque tubular member coaxially surrounding said cylindrical optical fiber array, said opaque tubular member having a longitudinal aperture in the wall thereof, said longitudinal aperture overlying at least a portion of a diffuser tip.

4. The intra-vascular catheter of claim 2 wherein said means for directing the narrow beam of light from the diffuser tip portion radially outward from the diffuser tip portion to illuminate a target and receive fluorescence light from the target comprises a rotatable opaque tubular member coaxially surrounding said cylindrical optical fiber array, said opaque tubular member having a longitudinal aperture in the wall thereof, said longitudinal aperture overlying at least a portion of the diffuser tip portion.

5. A device for intra-vascular optical radial imaging comprising a guidewire compatible intra-vascular catheter having a distal end dimensioned for insertion into a patient's blood vessel and a proximal end and a tubular body portion therebetween, said body portion comprising a plurality of coaxial concentric tubular members in which:
   (a) the outermost tubular member is an optically transparent sheath;
   (b) an optically opaque tube underlies said optically transparent sheath, said optically opaque tube being rotatably mounted to permit the opaque tube to spin, the opaque tube having an aperture in the wall thereof;
   (c) an optically transmissive member having a diffuser tip in optical communication therewith underlies said spinning tube; and
   (d) an optically reflective center tube underlies said optically transmissive member, the inner walls of which center tube form a guidewire lumen, said optically opaque tube being spaced from said overlying optically transparent sheath and said underlying optically transmissive member by an air space, said air space being maintained by at least two cylindrical spacer bearings surrounding said optically opaque tube.

6. A method of imaging tissue on the interior wall of a tubular member comprising the steps of:
   (a) inserting the distal end of a guidewire into said tubular member until the distal end is adjacent to the tissue to be imaged;
   (b) inserting the distal end of the intra-vascular catheter of claim 1 over the guidewire and advancing the catheter into the vessel until the distal tip of the catheter is adjacent to the tissue to be imaged;
   (c) continuously sweeping a narrow illuminating beam of light over the surrounding tissue in to induce fluorescence therein; and
   (d) collecting the fluorescence light emanating from the illuminated tissue and measuring the wavelength and amplitude of the fluorescence light.

7. A method for imaging tissue on the interior wall of a tubular member comprising the steps of:
   (a) inserting the distal end of a guidewire into said tubular member until the distal end is adjacent to the tissue to be imaged;
   (b) inserting the distal end of the intra-vascular catheter of claim 2 over the guidewire and advancing the catheter into the vessel until the distal tip of the catheter is adjacent to the tissue to be imaged;
   (c) continuously sweeping a narrow beam of illuminating radially the surrounding tissue in discrete increments to induce fluorescence; and
   (d) collecting the fluorescence light from the illuminated tissue and measuring the wavelength and amplitude of the fluorescence signal.

* * * * *